United States Patent
Krogh Andersen

(10) Patent No.: US 9,717,862 B2
(45) Date of Patent: Aug. 1, 2017

(54) INFUSION FLUID WARMER

(71) Applicant: MEQU APS, Hellerup (DK)

(72) Inventor: Ulrik Krogh Andersen, Hellerup (DK)

(73) Assignee: Mequ ApS, Hellerup (DK)

( * ) Notice: Subject to any disclaimer, the term of this patent is extended or adjusted under 35 U.S.C. 154(b) by 191 days.

(21) Appl. No.: 14/351,388

(22) PCT Filed: Oct. 8, 2012

(86) PCT No.: PCT/EP2012/069887
§ 371 (c)(1),
(2) Date: Apr. 11, 2014

(87) PCT Pub. No.: WO2013/053674
PCT Pub. Date: Apr. 18, 2013

(65) Prior Publication Data
US 2014/0276545 A1  Sep. 18, 2014

Related U.S. Application Data

(60) Provisional application No. 61/546,779, filed on Oct. 13, 2011.

(51) Int. Cl.
A61M 5/00 (2006.01)
A61M 5/44 (2006.01)
(Continued)

(52) U.S. Cl.
CPC ............ A61M 5/44 (2013.01); H05B 3/16 (2013.01); H05B 3/20 (2013.01); A61M 5/445 (2013.01);
(Continued)

(58) Field of Classification Search
CPC ............ A61M 5/44; A61M 2205/3653; A61M 2205/127; A61M 5/445; A61M 1/166;
(Continued)

(56) References Cited

U.S. PATENT DOCUMENTS 4,293,762 A * 10/1981 Ogawa .................... A61M 5/44
165/46
4,478,076 A * 10/1984 Bohrer .................. G01F 1/6845
73/204.16
(Continued)

FOREIGN PATENT DOCUMENTS

CN    2758247 Y     2/2005
CN    101612425 A   12/2009
(Continued)

OTHER PUBLICATIONS

Office Action dated Jul. 23, 2015 for Chinese Application 201280058074.X.

Primary Examiner — Kevin C Sirmons
Assistant Examiner — William Carpenter
(74) Attorney, Agent, or Firm — Peter A. Nieves; Sheehan Phinney Bass & Green PA

(57) ABSTRACT

The present invention relates in one aspect to an infusion fluid warmer which comprises a casing shell having an upper wall structure and a lower, opposing, wall structure. The casing shell encloses a fluid channel or passage extending through the casing shell in-between the upper and lower wall structures and fluid inlet and outlet ports coupled to opposite ends of the fluid channel or passage to allow a flow of infusion fluid through the casing shell. A housing shell is formed in a thermally conducting and electrically insulating material and a heating element is bonded to the housing shell and thermally coupled thereto. The fluid channel or passage extends through the housing shell or extends around the housing shell such that heat energy is transferred to the infusion fluid by direct physical contact with housing shell material.

14 Claims, 6 Drawing Sheets

(51) Int. Cl.
*H05B 3/16* (2006.01)
*H05B 3/20* (2006.01)

(52) U.S. Cl.
CPC ............ *A61M 2205/3368* (2013.01); *A61M 2205/3653* (2013.01); *A61M 2205/8206* (2013.01); *H05B 2203/002* (2013.01); *H05B 2203/021* (2013.01)

(58) Field of Classification Search
CPC ............ A61M 1/369; H05B 2203/002; H05B 2203/003; H05B 2203/004; H05B 2203/009; H05B 2203/001; F24H 1/101; F24H 1/102
See application file for complete search history.

(56) References Cited

U.S. PATENT DOCUMENTS

| | | | | |
|---|---|---|---|---|
| 4,574,876 A * | 3/1986 | Aid | ............ | A61M 5/44 165/170 |
| 4,680,445 A * | 7/1987 | Ogawa | ............ | A61M 5/44 165/46 |
| 4,735,609 A | 4/1988 | Comeau | | |
| 5,245,693 A * | 9/1993 | Ford | ............ | A61M 5/44 165/169 |
| 6,146,359 A * | 11/2000 | Carr | ............ | A61B 18/18 219/687 |
| 6,175,688 B1 * | 1/2001 | Cassidy | ............ | A61M 5/44 392/470 |
| 6,788,885 B2 * | 9/2004 | Mitsunaga | ............ | A61M 5/44 392/470 |
| 7,132,627 B2 * | 11/2006 | Peyronny | ............ | F24H 7/002 219/530 |
| 7,865,072 B2 * | 1/2011 | Cassidy | ............ | A61M 5/44 392/470 |
| 2002/0181948 A1 * | 12/2002 | Akahane | ............ | A61F 7/0085 392/470 |
| 2005/0008354 A1 * | 1/2005 | Cassidy | ............ | A61M 5/44 392/494 |
| 2008/0077087 A1 | 3/2008 | Martens | | |
| 2010/0222740 A1 * | 9/2010 | Park | ............ | A61M 5/44 604/114 |
| 2014/0072288 A1 * | 3/2014 | Newell | ............ | A61M 5/44 392/484 |

FOREIGN PATENT DOCUMENTS

| | | |
|---|---|---|
| CN | 101947339 A | 1/2011 |
| CN | 201592444 U | 1/2011 |
| CN | 201692416 U | 1/2011 |
| CN | 201692430 U | 1/2011 |
| CN | 201692445 U | 1/2011 |
| CN | 201692448 U | 1/2011 |
| CN | 201701577 U | 1/2011 |
| CN | 201701585 U | 1/2011 |
| CN | 201701586 U | 1/2011 |
| CN | 201710765 U | 1/2011 |
| CN | 201710766 U | 1/2011 |
| CN | 201719650 U | 1/2011 |
| CN | 201727734 U | 2/2011 |
| CN | 201727808 U | 2/2011 |
| CN | 201727809 U | 2/2011 |
| CN | 201735015 U | 2/2011 |
| CN | 201744029 U | 2/2011 |
| CN | 201755349 U | 3/2011 |
| CN | 201759946 U | 3/2011 |
| CN | 201768233 U | 3/2011 |
| CN | 201768234 U | 3/2011 |
| CN | 201783036 U | 4/2011 |
| CN | 201791194 U | 4/2011 |
| CN | 201798977 U | 4/2011 |
| CN | 102058919 A | 5/2011 |
| CN | 201314947 U | 5/2011 |
| CN | 201832201 U | 5/2011 |
| CN | 102105188 A | 6/2011 |
| CN | 201862059 U | 6/2011 |
| CN | 201862080 U | 6/2011 |
| CN | 201838972 U | 7/2011 |
| CN | 201888973 U | 7/2011 |
| EP | 1066844 A1 | 2/2001 |
| EP | 2311514 A2 | 4/2011 |
| EP | 2366419 A1 | 9/2011 |
| JP | H09-500481 | 1/1997 |
| JP | 2007527495 | 9/2007 |
| JP | 2011024626 A | 2/2011 |
| RU | 2009133512 A | 3/2011 |
| WO | 9503680 | 2/1995 |
| WO | 9709076 A1 | 3/1997 |
| WO | 0162194 A1 | 8/2001 |
| WO | 03049790 A1 | 6/2003 |
| WO | 2005009500 | 2/2005 |
| WO | 2011022115 A1 | 1/2011 |
| WO | 2011015912 A1 | 2/2011 |
| WO | 2011015961 A1 | 2/2011 |
| WO | 2011034866 A1 | 2/2011 |
| WO | 2011035238 A2 | 3/2011 |
| WO | 2011054453 A1 | 3/2011 |
| WO | 2011045011 A1 | 4/2011 |
| WO | 2011152767 A1 | 6/2011 |
| WO | 2011169343 A1 | 7/2011 |
| WO | 2011097487 A2 | 8/2011 |
| WO | 2011194846 A1 | 8/2011 |
| WO | 2011198343 A1 | 8/2011 |
| WO | 2011202034 A1 | 8/2011 |
| WO | 2011113421 A2 | 9/2011 |
| WO | 2011229615 A1 | 9/2011 |

* cited by examiner

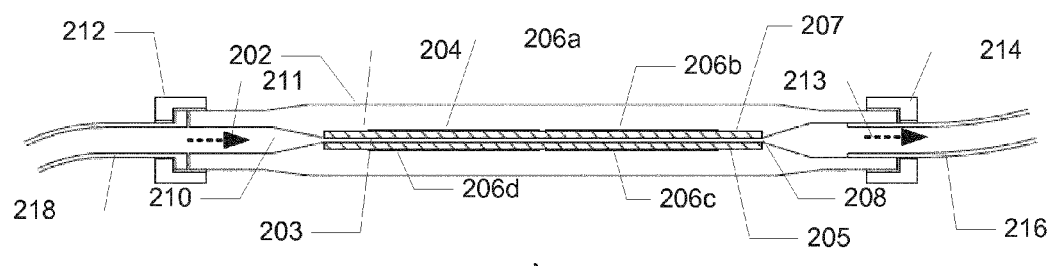
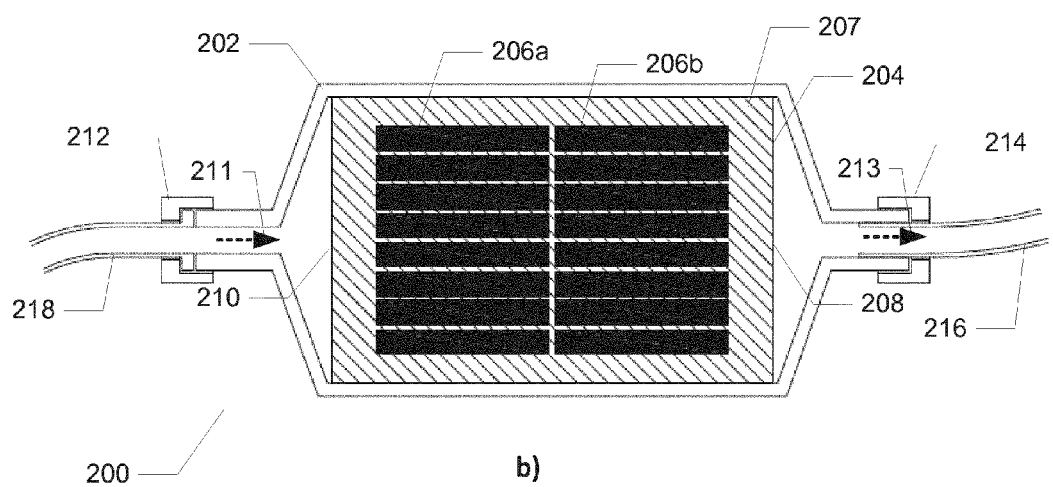
Figs. 2 a)-b)

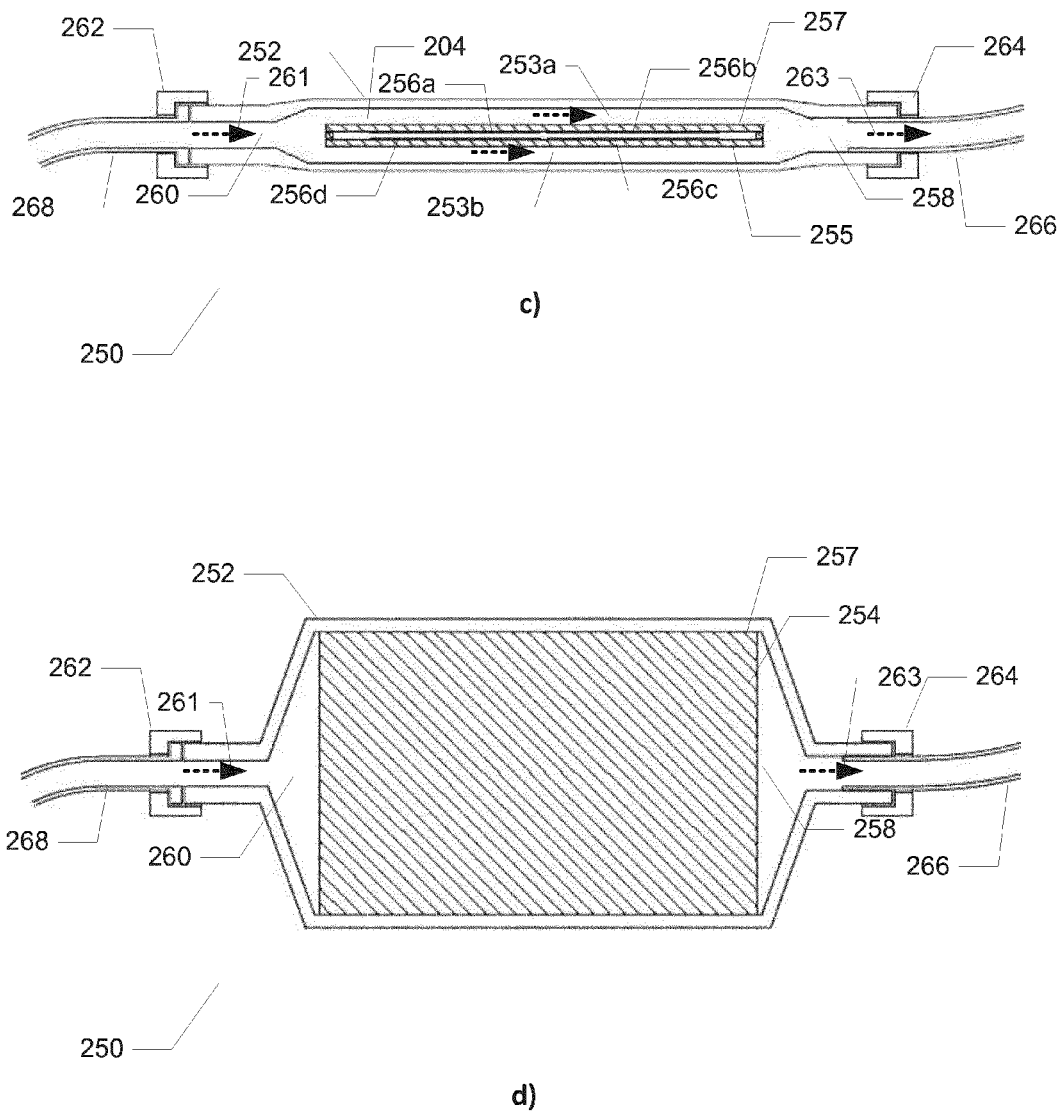
Figs. 2 c)-d)

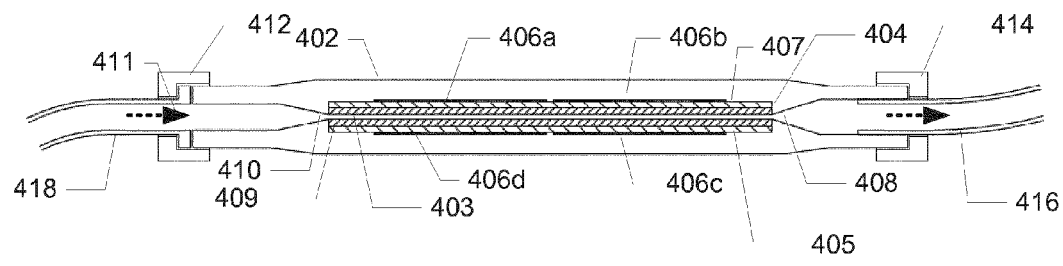
a)
400
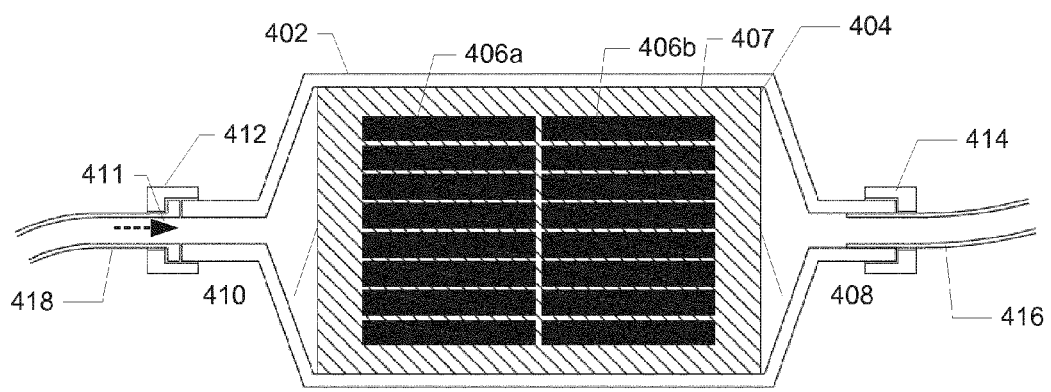
b)
Fig. 4

INFUSION FLUID WARMER

CROSS-REFERENCE TO RELATED APPLICATIONS

The present application is the National State Entry of PCT/EP2012/069887, filed on 11 Apr. 2014, which claims the benefit of U.S. Provisional Application No. 64/546,779, filed on 13 Oct. 2011.

The present invention relates in one aspect to an infusion fluid warmer which comprises a casing shell having an upper wall structure and a lower, opposing, wall structure. The casing shell encloses a fluid channel or passage extending through the casing shell in-between the upper and lower wall structures and fluid inlet and outlet ports coupled to opposite ends of the fluid channel or passage to allow a flow of infusion fluid through the casing shell. A housing shell is formed in a thermally conducting and electrically insulating material and a heating element is bonded to the housing shell and thermally coupled thereto. The fluid channel or passage extends through the housing shell or extends around the housing shell such that heat energy is transferred to the infusion fluid by direct physical contact with housing shell material.

BACKGROUND OF THE INVENTION

Intravenous or infusion fluid such as blood is commonly used in hospitals and in the field for example in emergency or war zones. The infusion fluid is important for virtually all medical procedures and applications. Such infusion is typically delivered from an IV fluid bag or container into a blood vessel of a patient. It is desirable to warm the blood or IV fluid to a certain range of temperature (e.g. between 36 and 37 degrees Celsius) to avoid temperature drop in the patient which may lead to hypothermia.

There exist various conventional devices and techniques for heating or warming infusion fluids before being administrated to a patient. However, these conventional devices and techniques suffer from a number of drawbacks. The conventional infusion fluid warmers are bulky and heavy which make them unsuited for portable applications where they have to be transported by foot for example by soldiers, rescue workers or ambulance crews to reach inaccessible emergency sites. The heavy and bulky nature of existing infusion fluid warmers also makes it difficult or impossible to secure or attach these to the patient's body in a convenient and safe manner. Another disadvantage of existing fluid warmers is that they are composed of a large number of separate parts which make them expensive to manufacture and tend to reduce reliability due to a multitude of separate engaging parts.

Yet another disadvantage of existing fluid warmers is a lack of a mechanism for capturing and coupling heat energy dissipated in the energy source during fluid warming to the infusion fluid. This leads to inefficient use of energy stored in the energy source, such as rechargeable or non-rechargeable batteries, and therefore a need for larger, heavier and more costly energy sources than strictly required to warm a given volume or amount of infusion fluid. According to one aspect of the present invention, this problem is solved by conducting excess heat energy generated by a portable energy source to the infusion fluid to heat the latter. Thus, ensuring that the energy held in the portable energy source is put to efficient use.

WO 2003/049790 A1 describes a system for heating transfusion fluids comprising a fluid warmer having an inlet channel and an outlet channel. A fluid passage of meandering shape is formed in a separate cartridge arranged between a pair of heat contact plates.

SUMMARY OF THE INVENTION

A first aspect of the invention relates to an infusion fluid warmer which comprises a casing shell having an upper wall structure and a lower, opposing, wall structure. The casing shell enclosing:
- a fluid channel or passage extending through the casing shell in-between the upper and lower wall structures,
- fluid inlet and outlet ports coupled to opposite ends of the fluid channel or passage to allow a flow of infusion fluid through the casing shell. A housing shell is formed in a thermally conducting and electrically insulating material and a heating element is bonded to the housing shell and thermally coupled thereto. The fluid channel or passage extends through the housing shell or extends around the housing shell such that heat energy is transferred to the infusion fluid by direct physical contact with housing shell material. The casing shell of the infusion fluid warmer may comprise a thermoplastic material or elastomeric compound fabricated by a suitable manufacturing process such as injection moulding. The casing shell may function to protect the housing shell from mechanical shock, impacts and pollutants in the external environment. The casing shell may have a shape with rectangular, elliptical or circular cross-sectional profile, i.e. along a cross-section transversal to the direction of infusion fluid flow at the fluid inlet and outlet ports.

The fluid inlet and outlet ports of the casing shell allow the infusion fluid to flow through the infusion fluid warmer with cold or unheated infusion fluid entering at the inlet port and heated or warmed infusion fluid exiting through the outlet port on its way to the patient.

The housing shell possesses an advantageous multi-purpose role in the present infusion fluid warmer by acting as a physical carrier for the heating element bonded thereto, e.g. thick film and/or thin film resistor(s), and as a heat exchanger or heat plate transmitting heat energy directly to the infusion fluid by the physical contact between the housing shell material and the fluid. This property is capable of providing a compact infusion fluid warmer requiring only a minimum of separate parts to be manufactured and assembled. The housing material preferably comprises ceramic material such as Aluminium Oxide ($Al_2O_3$), Aluminum Nitrate or Beryllium Oxide which all are well-suited as substrate materials for a large range of heating element materials, in particular thick film and thin file resistors. The ceramic material additionally possesses good thermal conductivity and good electrically insulating properties. The skilled person will appreciate that the material of the housing shell is preferably bio-compatible for example a bio-compatible ceramic material such as Aluminium oxide ($Al_2O_3$) due to its direct contact with the infusion fluid to be distributed to the patient. Alternatively, materials that are not bio-compatible may be used such as ceramics Aluminum Nitrate or Beryllium Oxide.

To possess adequate electrically insulating properties, the housing shell preferably comprises a material with specific electrical resistance larger than $1 \times 10^9$ ohm*m, to meet official requirements. To possess adequate thermally conducting properties, the housing shell is preferably made of a material with specific thermal conductivity larger than 0.5

W/(m·K), more preferably larger than 1.0 W/(m·K) even more preferably larger than 10.0 W/(m·K).

The housing shell may be fabricated as a single unitary element for example by moulding or machining a solid object. The fluid channel may have a largely straight rectangular form extending through a central portion of the element. In alternative embodiments, the housing shell comprises a plurality of separate structures that are bonded together after individual fabrication for example by gluing, soldering, press-fitting, welding etc. In one such embodiment, the housing shell comprises an upper wall structure and a lower wall structure formed in separate upper and lower housing shells, the upper and lower housing shells being bonded to each other. In this embodiment, the fluid channel may extend in-between the upper and lower housing shells for example formed by mating grooves or trenches formed in facing surfaces of the upper and lower wall structures of the housing shell to form a fluid passage extending through the housing shell. The fluid channel may have a variety of different shapes but preferably a shape that maximizes a contact area between the infusion fluid and the housing shell (functioning as a heat exchanger) to increase the fluid heating capacity of the fluid warmer (for example expressed in liters per minute). In one embodiment, the fluid channel has a meandering shape in a cross-sectional plane extending perpendicularly to the flow of infusion fluid at the inlet and outlet ports. This plane may be orthogonally to a longitudinal axis of the housing shell if the latter has a flat plate like structure. In an alternative embodiment, the fluid channel comprises a substantially straight channel extending along the longitudinal axis of the plate shaped housing shell. In the latter embodiment, the fluid channel preferably extends through a substantial portion of a width of the housing shell to maximise the contact area between the infusion fluid and the housing shell. The fluid channel may be formed as a substantially rectangular straight tunnel with a height between 0.1 mm and 5 cm such as between 0.5 mm and 2 cm. If the housing shell has the flat plate shaped structure, its height may be less than 4.0 cm, preferably less than 1.0 cm.

In yet another embodiment of the infusion fluid warmer, the fluid channel extends around the housing shell such that the fluid channel comprises a first channel segment arranged between the upper wall structure of the housing shell and the upper wall structure of the casing. The fluid channel further comprises a second channel segment arranged between the lower wall structure of the housing shell and the lower wall structure of the casing. In this embodiment, the upper and the lower wall structure of the housing shell are both in physical contact with the infusion fluid to provide a large contact area between the housing shell and infusion fluid so as to ensure efficient transfer of heat energy. The skilled person will appreciate that the fluid channel in the alternative may comprise only a single channel segment extending around the housing shell.

The heating element is preferably bonded to a surface of the upper and/or a surface of the lower wall structure facing away from the fluid channel to isolate electrical drive voltages or currents supplied to the heating element from the infusion fluid and prevent corrosion attacks on electrical terminals or components of the heating element. In one such embodiment, the heating element comprises a thin film resistor or a thick film resistor bonded directly on the surface(s) of the upper and/or lower wall structures facing away from the fluid channel for example by screen-printing or other suitable bonding mechanism. Hence, in these embodiments, the electrically insulating property of the upper and lower wall structure(s) is used to electrically insulate the infusion fluid from the DC or AC voltage/current applied to heating element or elements to heat these. The thick film resistor or thin film resistor may naturally comprise a plurality of resistor elements or individual resistors coupled in series or parallel to provide any desired resistance value depending on the requirement of the application. The thick film or thin resistor may cover a considerable portion of the total area of the surface of the upper wall structure facing away from the fluid channel and/or a considerable portion of the total area of the outer surface of the lower wall structure facing away from the fluid channel. The total resistance of the thick film or thin film resistor may vary widely e.g. from 0.001 ohm to 10 Kohm. The thermally conducting property of the upper wall structure and the lower wall structure ensure that heat energy dissipated in the thick film resistor is efficiently conducted to the fluid channel. The surface of the upper and lower wall structures facing away from the fluid channel may comprise a pair of electrical coupling terminals for receipt of electrical power to the thick film or thin film resistor.

According to a preferred embodiment of the invention, the heating element comprises a portable energy source such as rechargeable, non-rechargeable batteries, a super capacitor etc. enclosed between the upper and lower wall structures of the housing shell. This embodiment provides a fully portable infusion fluid warmer which can be used in the field for example in emergency or war zones allowing infusion of fluids such as blood without cooling the patient. The simplicity of the present infusion fluid warmer combined with the small size and low weight is a significant advantage for medical personnel transporting the warmer.

According to this embodiment, the portable energy source is thermally coupled to the fluid channel preferably by direct physical contact with the housing shell to thermally conduct heat energy dissipated in the portable energy source in connection with its depletion to the fluid channel and infusion fluid flowing there through. In this context "direct physical contact" means in contact without any intervening passage or layer of atmospheric air or other gaseous substances. The materials, shape and dimensions of the housing shell, the fluid channel and the portable energy source are preferably configured such that the thermal resistance between a housing of the portable energy source and the infusion fluid is less than 100° C./W, preferably less than 25° C./W, even more preferably less than 10° C./W.

The skilled person will appreciate that the heat energy dissipated in the portable energy source for example due to its internal impedance may exclusively be utilized to heat the infusion fluid or it may supplement heat energy dissipated in the heating element such as the above-discussed thick film or thin film resistor(s). Ion the latter case, both types of heat sources contribute to the heating of the infusion fluid. In this manner, the infusion fluid is warmed or heated by excess heat generated by the portable energy source instead of being wasted to the surrounding air. Consequently, efficient use is made of the energy stored in the portable energy source.

The housing shell may have a flat plate shaped structure with a height less than 2.0 cm, preferably less than 1.0 cm.

Another aspect of the invention relates to an infusion fluid warmer comprising a casing shell having an upper wall structure and a lower, opposing, wall structure. A fluid channel or passage extends through the casing shell in-between the upper and lower wall structures. Fluid inlet and outlet ports are coupled to opposite ends of the fluid channel or passage to allow a flow of infusion fluid through the casing shell. A heating element is thermally coupled to the fluid channel to transfer heat energy to the infusion fluid and the heating element comprises a portable energy source such as a rechargeable battery, a non-rechargeable battery, a super capacitor etc. This aspect of the invention provides a fully portable infusion fluid warmer for a variety of beneficial field uses for example in emergency or war zones allowing infusion of fluids or blood without cooling the patient. The simplicity of the portable infusion warmer combined with small size and low weight are noticeable advantages for the medical personnel transporting the warmer. The casing shell may comprise a thermoplastic material or elastomeric compound and fabricated by injection moulding. The casing shell may fully enclose or surround the heating element and the portable energy source to protect these from mechanical shocks and impacts and pollutants in the external environment. Because the portable energy source is thermally coupled to the fluid channel, heat energy dissipated therein, for example due to internal impedance of the portable energy source, is conveyed to the infusion fluid to heat of the infusion fluid instead of being wasted to the surrounding air. Consequently, energy stored in the portable energy source is put to efficient use which allows size, weight and energy storage capacity of the portable energy source to be reduced, or alternatively to provide higher energy storage capacity of the portable energy source for a given size, weight or capacity. The thermal coupling between the portable energy source energy source and the fluid channel is preferably provided by direct or indirect physical contact between these. In this context "direct or indirect physical contact" means in contact without any intervening passage or layer of atmospheric air or other gaseous substances such as through an electrically insulating and thermally conducting energy source housing as described below. A thermal resistance between the portable energy source and the infusion fluid is preferably less than 100° C./W, preferably less than 25° C./W, even more preferably less than 10° C./W.

The portable energy source is preferably enclosed in a surrounding electrically insulating and thermally conducting energy source housing which preferably is arranged inside the casing shell. In the latter embodiment, the energy source housing and the casing shell may be coaxially aligned to form a fluid channel surrounding the energy source housing for example on all sides. In the latter embodiment, the fluid channel extends around or encircles the entire perimeter of the energy source housing to maximize the transmission of heat energy from the portable energy source to the infusion fluid. At the same time, efficient liquid cooling of the portable energy source is achieved.

Each of the energy source housing and the casing shell may possess a substantially circular, elliptical or rectangular cross-sectional profile. The fluid channel may accordingly be formed in-between an outer surface of the energy source housing and the upper and lower wall structures of the casing shell. The skilled person will understand that the energy source housing may comprise anyone of the ceramic materials discussed above in connection with the material of the housing shell. The heating element may additionally comprise a thin film resistor or a thick film resistor bonded directly, for example by screen-printing, to a surface of the energy source housing facing away from the fluid channel.

The energy source housing may be formed by a shell or casing of the rechargeable or non-rechargeable battery or formed as a separate housing enclosing existing separate battery shell or shells to form a separate battery compartment.

Each of the infusion fluid warmers described above in connection with the first and second aspects of the invention may advantageously comprise a temperature sensor for determining a temperature of the infusion fluid in the fluid channel at a suitable location such as at or proximate to the outlet port. A controller circuit may be operatively coupled to the temperature sensor and to the heating element to control instantaneous power dissipation of the heating element. The controller circuit is adapted to adjust power dissipation in the heating element in accordance with a desired or target temperature of the infusion fluid based on temperature data from the temperature sensor. The controller circuit preferably comprises a programmable microprocessor such as a Digital Signal Processor and suitable program code or instructions implementing the control algorithm. The programmable microprocessor may be an off-the-shelf industry standard type of microprocessor, preferably comprising appropriate input and output ports and peripheral devices such as EEPROM or Flash memory. However, the skilled person will understand that the controller circuit alternatively may be implemented by appropriately configured programmable logic such as FPGA devices or hard-wired circuitry comprising combinatorial logic and memory integrated on an Application Specific Integrated Circuit (ASIC). The controller circuit is preferably bonded to the surface of the upper wall structure facing away from the fluid channel or the surface of the lower wall structure facing away from the fluid channel. The controller circuit may be arranged on the same surface of the upper or lower wall structure as the thick film resistor or resistor if sufficient surface area is available. The use of the housing shell as carrier of the control circuit in accordance with the above embodiments of the invention provides a further size reduction of the infusion fluid warmer and reduces the number of separate parts that must be assembled during manufacturing of these infusion fluid warmers. In some embodiments of the invention, the controller circuit comprises one or more semiconductor transistors and/or semiconductors diodes configured for delivering a modulated drive signal to the heating element to dissipate power therein. The semiconductor transistors may comprise one or more power MOS transistors or IGBTs. The controller circuit controls the semiconductor transistors to apply a PWM (Pulse Width Modulated) drive signal across the heating element, e.g. the thick film resistor(s), such that a known quantity of electrical power is dissipated in the heating element. The controller circuit may be adapted to adjust the amount of electrical power dissipated in the heating element by adjusting the duty cycle of the PWM drive signal. Excess heat energy dissipated in the one or more semiconductor transistors and/or semiconductors diodes of the controller circuit during operation of the heating element may also be transmitted to the fluid channel by bonding these semiconductors to the surface of the upper and/or lower wall structure facing away from the fluid channel. The excess heat energy is caused by resistive and capacitive parasitic losses in the one or more semiconductor transistors and/or semiconductors diodes.

The temperature sensor(s) may comprise a semiconductor based sensor(s) placed in the fluid channel for example at or close to the outlet port such that a temperature of the heated or warmed infusion fluid can be accurately measured. Infusion fluid temperature data may be transmitted to the controller circuit in digitally coded format or as an analogue voltage, charge or current signal that is sampled by an analogue to digital converter (A/D-converter) in the controller circuit.

An advantageous embodiment of the temperature sensor comprises a thick film resistor or thin film resistor, preferably a thick or thin film resistor of the heating element. Since the resistance of thick film resistors is strongly temperature dependent these are particularly useful for temperature sensing and the controller circuit may be adapted to measure the instantaneous resistance of the thick film resistor. The controller can subsequently determine the temperature of the resistor from the determined instantaneous resistance by a suitable computing algorithm or look-up table. Furthermore, if the thick film resistor and the upper or lower wall structure of the housing shell has good thermal contact with the fluid channel, the temperature of the thick film resistor is approximately the same as the temperature of the infusion fluid such that the resistor temperature is a good estimate of the infusion fluid temperature, possibly adjusted with a predetermined correction factor.

Another, third aspect of the invention relates to a method of warming infusion fluid during administration to a patient, comprising steps of:
providing an infusion fluid warmer according to any of the above described aspects and embodiments thereof,
fastening the infusion fluid warmer to the patient for example with a bracelet or tape,
connecting the outlet port to a Venflon or IV-catheter inserted in the patient's vein,
connecting the inlet port to a fluid bag or container comprising a volume of infusion fluid. If necessary, a short extension tube may be inserted between the outlet port and the Venflon or IV-catheter. Likewise, an extension tube may be coupled between the inlet port and the fluid bag or container.

The ability to manufacture the present infusion fluid warmers with very compact dimensions makes it possible to conveniently fasten the infusion fluid warmer directly on a patient's body for example on the leg or arm with a suitable adhesive device or substance such as tape, plaster, bandage, elastic band etc. This simplifies the fluid delivery process and minimizes risk of accidental detachment.

BRIEF DESCRIPTION OF THE DRAWINGS

Preferred embodiments of the invention will be described in more detail in connection with the appended drawings, in which.

DETAILED DESCRIPTION OF PREFERRED EMBODIMENTS

Figure 1:
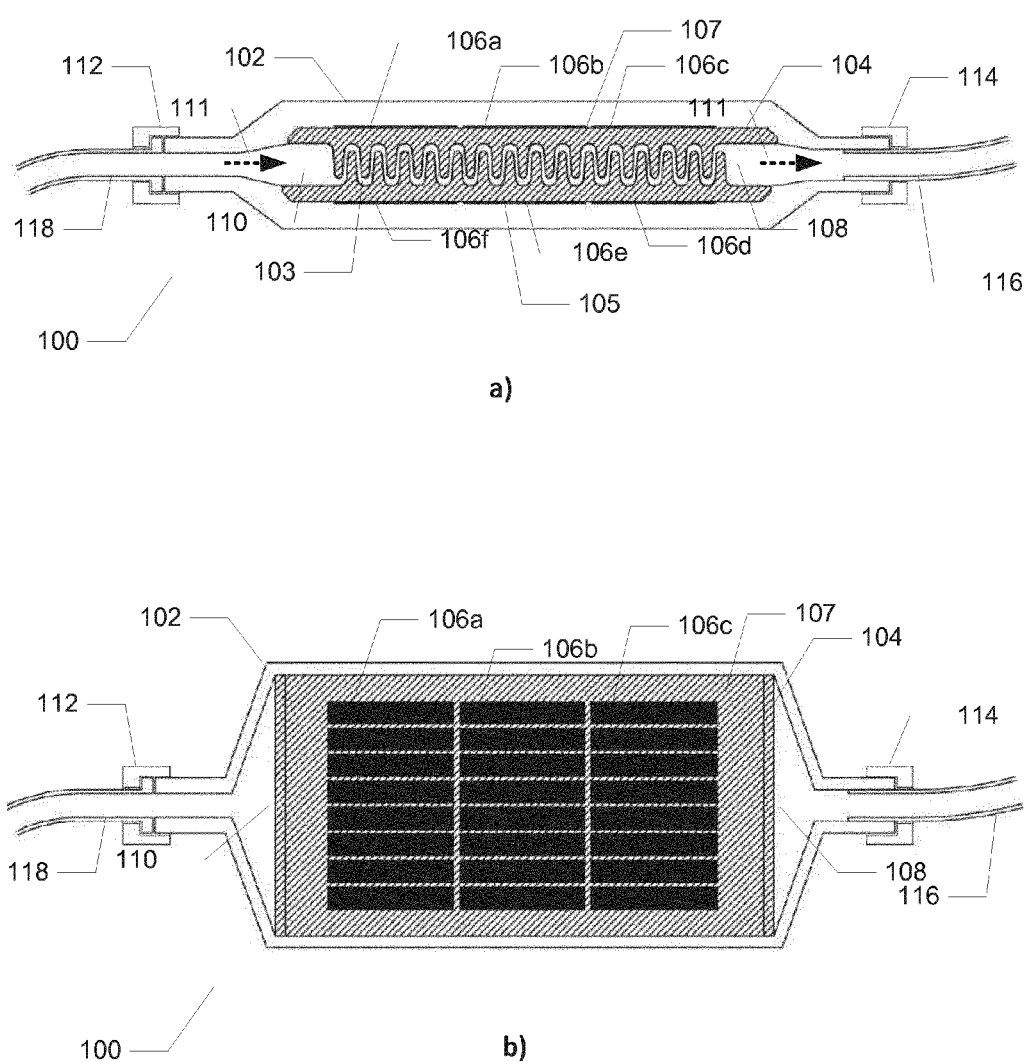
FIGS. 1a) and 1b) show a vertical cross-sectional view, and a horizontal top view, respectively, of an infusion fluid warmer in accordance with a first embodiment of the invention, FIGS. 2a) and 2b) show a vertical cross-sectional view and a horizontal top view, respectively, of an infusion fluid warmer in accordance with a second embodiment of the invention, FIGS. 2c) and 2d) show a vertical cross-sectional view and a horizontal top view, respectively, of an infusion fluid warmer in accordance with a third embodiment of the invention, FIGS. 3a) and 3b) show a vertical cross-sectional view and a horizontal top view, respectively, of an infusion fluid warmer in accordance with a fourth embodiment of the invention, FIGS. 4a) and 4b) show a vertical cross-sectional view and a horizontal top view, respectively, of an infusion fluid warmer in accordance with a fifth embodiment of the invention.

FIG. 1a) shows a vertical cross-sectional view of an infusion fluid warmer 100 in accordance with a first embodiment of the invention. The infusion fluid warmer 100 comprises a housing shell 104 formed in a thermally conducting and electrically insulating material, preferably comprising a ceramic material such as Aluminium Oxide ($Al_2O_3$). The dimensions of the housing shell 104 may vary in accordance with specific requirements for the infusion fluid warmer 100, in particular its fluid warming capacity.

The housing shell 104 is encapsulated or enclosed within an outer casing 102 which may be formed in a suitable polymeric material for example a thermoplastic material or elastomeric compound by injection moulding. The outer casing 102 may be shaped and sized to protect the housing shell 104 from mechanical shocks and impacts. A pair of cap nuts or caps 112, 114 covers respective entrance openings of the outer casing 102 and is preferably used to seal or isolate the interior volume of the outer casing 102 from liquids, dust and other pollutants in the external environment. A prototype of the depicted infusion fluid warmer 100 was produced with a outer casing 102 with a 5.1 cm length, 3.3 cm width and thickness of 2.1 cm. The housing shell 104 has a plate-shaped form comprises an upper wall structure 107 and a lower, opposing, wall structure 105 divided by a fluid channel or passage 103 of meandering shape projecting in a vertical plane, i.e. a plane perpendicularly to the horizontal plane parallel with the outer surfaces of the housing shell 104. The fluid channel 103 extends through the housing shell 104 in-between the upper and lower wall structures, 105, 107, respectively. In the present embodiment, the upper wall structure 107 and the lower wall structure 105 are formed in separate upper and lower housing shells bonded to each other by suitable means such as gluing, soldering, press-fitting, welding etc. A fluid channel 103 extends between a fluid inlet port 110 and a fluid output port 108 to allow a flow of infusion fluid through the housing shell 104. The fluid inlet port 110 is coupled to a first end of the fluid channel 103 and the fluid output port coupled to an opposite end of the fluid channel 103. The fluid channel has a meandering shape in the depicted vertical cross-sectional plane extending substantially perpendicularly to a flow of infusion fluid (indicated by arrows 111) at the inlet and outlet ports 110, 108, respectively. Cold or unheated infusion fluid such as blood or IV solution flows from a fluid source such as fluid bag through an IV line or tube 118 through the fluid inlet port 110, through the fluid channel 103 at out of the fluid outlet port 108. From the fluid outlet port 108, heated or warmed infusion fluid flows through the IV line or tube 116 towards an IV-catheter (e.g. Venflon) inserted in a patient's vessel for the purpose of intravenous therapy.

The meandering shape of the fluid channel 103 is made by a pair of mating grooves or trenches formed in the upper and lower wall structures, 107, 105, respectively, of the housing shell 104. Heat energy is therefore transferred to the infusion fluid in the fluid channel 103 by direct contact with the heated wall structures of the housing shell 104. The use of a bio-compatible ceramic material like Aluminium Oxide allows the infusion fluid to be in direct physical contract with the housing shell material in the fluid channel 103 and ensures efficient heat transfer together with a simplified structure of the infusion fluid warmer with few separate parts. An array of thick film resistors 106a-106f acts like a heating element of the infusion fluid warmer 100 and are screen-printed on surfaces of the upper and lower wall structures, 105, 107, respectively facing away from the fluid channel 103. Through application of a PWM (Pulse Width Modulated) drive signal across the array thick film resistors, electrical power is dissipated therein so as to heat the thick film resistors as explained in further detail below. Thick film resistors 106a, 106b and 106c are screen-printed on an outer surface of the upper wall structure 107 facing oppositely to the fluid channel 103 and thick film resistors 106d, 106e and 106f are screen-printed on an outer surface of the lower wall structure 107 facing oppositely to the fluid channel 103. Since the array of thick film resistors 106a-106f are in good physical contact with the upper and lower wall structures, 107, 105, respectively, without any intervening air gaps efficient thermal coupling is provided to infusion fluid flowing in the fluid channel 103 such that heat energy is transferred to the infusion fluid to warm the fluid. The thick film resistors preferably cover a large portion of the respective outer surface areas which ensure a good thermal coupling between the resistors and the upper and lower wall structures, 105, 107, respectively, of the housing shell 104. The total resistance of the array of thick film resistors 106a-106f as seen by the PWM (Pulse Width Modulated) drive signal preferably lies between 0.001 ohm and 6250 ohm such as between 0.1 ohm and 1 Kohm ($10^3$ ohm).

The properties of the ceramic material used for the housing shell 104 in the present embodiment, lead to several significant advantages. One advantage is that the ceramic material has good thermal conductivity such that heat energy produced in the heating element (i.e. the thick film resistor array) is transferred to the infusion fluid with low energy loss. The ceramic material furthermore serves as a carrier of the heating element itself and finally serves as an electrical insulator insulating the PWM voltage applied to the heating element from the infusion fluid and therefore from the patient.

The infusion fluid warmer 100 preferably comprises a temperature sensor (not shown) for determining a temperature of the infusion fluid in the fluid channel 103 for example at the outlet port 108 to ascertain the infusion fluid temperature lies within a certain allowable range for example between 36 and 37 degree Celsius. A controller circuit (not shown) is operatively coupled to the temperature sensor and to the array of thick film resistors 106a-106f to control instantaneous power dissipation in the array. The instantaneous power dissipation in the array of thick film resistors 106a-106f is preferably controlled by adjusting a duty cycle of the previously mentioned PWM drive signal applied to the resistor array in accordance with a desired or target temperature of the infusion fluid. The adjustment may for example be effected through a suitable feedback loop and control algorithm executed by the controller circuit based on temperature data from the temperature sensor. The controller circuit preferably comprises a programmable microprocessor such as a Digital Signal Processor and suitable program code or instructions implementing the control algorithm. The programmable microprocessor may be an off-the-shelf industry standard type of microprocessor, preferably comprising appropriate input and output ports and peripheral devices such as EEPROM or Flash memory. However, the skilled person will understand that the controller circuit alternatively may be implemented by appropriately configured programmable logic such as FPGA devices or hard-wired circuitry comprising a combination of combinatorial logic and memory integrated on an Application Specific Integrated Circuit (ASIC). The controller circuit is preferably bonded to the outer surface of the upper wall structure 107 or the outer surface of the lower wall structure 105 such that it is arranged adjacent to the thick film resistors 106a, 106b and 106c (please refer to FIG. 1b)) or the thick film resistors 106d, 106e and 106f. In this manner, the upper wall structure 107 or the lower wall structure 105 also functions a carrier for the controller circuit and may be thermally coupled thereto such that heat energy dissipated in the controller can be directed through the housing shell 104 to the infusion fluid. The controller circuit is preferably powered by rechargeable or non-rechargeable batteries such that the entire infusion fluid warmer 100 is portable. In the alternative, the controller circuit may be energized by a mains operated power supply such as a switched mode power supply.

FIG. 1b) shows a top view of the infusion fluid warmer 100 in accordance with the first embodiment of the invention. The lid, or upper wall of the thermoplastic casing 102 has been removed such that the surface of the upper wall 107 facing away from the fluid channel of the housing shell 104 is visible. The thick film resistors 106a, 106b and 106c are disposed on the outer surface of the upper wall 107 covering a large portion of the available surface area as previously mentioned. Each of the thick film resistors 106a, 106b and 106c comprises a plurality of resistor segments arranged below each other. These resistor segments may be coupled in series or parallel to provide a desired resistance value of the thick film resistor. The skilled person will understand that the plurality of resistor segments could be replaced with a single resistor of equivalent resistance. Likewise, the thick film resistors 106a, 106b and 106c could be replaced with a single resistor of equivalent resistance. As illustrated, a peripheral edge portion is left uncovered by the thick film resistors 106a, 106b and 106c and may be used for attachment of the controller circuit providing a very compact and mechanical robust overall structure with individual components placed in good thermal contact.

FIG. 2a) shows a vertical cross-sectional view of an infusion fluid warmer 200 in accordance with a second embodiment of the invention. Similar features in the present and the above-described first embodiment of the infusion fluid warmer have been provided with corresponding reference numerals to ease comparison. The infusion fluid warmer 200 comprises a housing shell 204 formed in a thermally conducting and electrically insulating material, preferably comprising a ceramic material such as Aluminium Oxide ($Al_2O_3$). The dimensions of the housing shell 204 may vary in accordance with specific requirements for the infusion fluid warmer 200, in particular its fluid warming capacity. The housing shell 204 is encapsulated or enclosed within an outer or exterior casing shell 202 held together by an associated pair of cap nuts or caps 212, 214. The latter may be formed in one of the previously described materials and for the same purpose. The exterior casing shell 202 comprises a fluid inlet port 210, where the infusion fluid enters (illustrated by arrow 211), and an oppositely arranged fluid outlet port 208, where the infusion fluid exits (illustrated by arrow 213), during operation of the infusion fluid warmer 200

The housing shell 204 has a plate-shaped form which comprises the upper wall structure 207 and the lower, opposing, wall structure 205 separated by a fluid channel or passage 203 extending between facing surfaces of the upper and lower wall structures 207, 205. In the present embodiment, the upper wall structure 207 and the lower wall structure 205 are formed in separate upper and lower housing shells which have been bonded to each other after fabrication by suitable means such as gluing, soldering, press-fitting, welding etc. The fluid channel 203 has a substantially straight horizontal shape in the present embodiment compared to the meandering shape in the above-described first embodiment of the present infusion fluid warmer. The fluid channel 203 preferably extends below a substantial portion of the facing surfaces of the upper and lower wall structures 207, 205 to maximize a flow rate of the infusion fluid flow through the fluid channel 203. Likewise, the direct physical contact area between the infusion fluid and the upper and lower wall structures 207, 205 through the facing surfaces is maximized to improve direct heat energy transfer to the infusion fluid through the upper and lower wall structures 207, 205. The height of the fluid channel 203 preferably lies between 0.1 mm and 5 cm. A significant advantage of the straight channel or passage design chosen for the present embodiment is a smaller pressure drop. The fluid channel 203 may comprise a plurality of vertical pillars mechanically connecting the upper wall structure 207 and the lower wall structure 205 to improve the mechanical strength of the housing shell 204, in particular the strength to vertically oriented shocks.

An array of thick film resistors 206a-206d acts as a heating element of the infusion fluid warmer 200. The array of thick film resistors 206a-206d is screen-printed, or firmly bonded or attached with an alternative fasting mechanism, on surfaces of the upper and lower wall structures, 207, 205, respectively, facing away from the fluid channel 203. The array of thick film resistors is preferably bonded to the outer surfaces of the upper and lower wall structures 207, 205 such that efficient thermal coupling, i.e. low thermal resistance, is achieved to the wall structures and therefore also to the infusion fluid flowing in the fluid channel 203. The individual resistors of the array of thick film resistors are preferably arranged in abutment with the wall structure in question without any intervening air gap. In this manner, heat energy dissipated in the array of thick film resistors 206a-206d is efficiently transferred to the infusion fluid to warm the fluid. The thick film resistors preferably cover a large portion of the respective surface areas which also ensure good thermal coupling between the thick film resistors and the upper and lower wall structures 207, 205 respectively, of the housing shell 204. The total resistance of the array of thick film resistors 206a-206d as seen by a drive signal such as a PWM (Pulse Width Modulated) drive signal preferably lies between 0.001 ohm and 6250 ohm such as between 0.1 ohm and 1 k$\Omega$ ($10^3$ ohm).

The infusion fluid warmer 200 may comprise a temperature sensor (not shown) for determining a temperature of the infusion fluid in the fluid channel 203 for example at the outlet port 208. The temperature sensor may be utilized to ascertain the infusion fluid temperature lies within a certain allowable range for example between 36 and 37 degree Celsius. A controller circuit (not shown) is operatively coupled to the temperature sensor and to the array of thick film resistors 206a-206d to control instantaneous power dissipation in the array in the same manner as described above in connection with the first infusion fluid warmer embodiment 100.

The skilled person will appreciate the firm bonding between the array of thick film resistors 206a-206d and the housing shell 204 provides a compact unitary assembly of heating element and heat exchanger with a low parts count in the present infusion fluid warmer 200.

FIG. 2b) shows a top view of the infusion fluid warmer 200 in accordance with the second embodiment of the invention. The lid or upper wall of the thermoplastic casing 202 has been removed such that the outer surface of the upper wall 207 of the housing shell 204 is exposed. The thick film resistors 206a, 206b are disposed on the outer surface of the upper wall 207 covering a large portion of the available surface area. Each of the thick film resistors 206a, 206b comprises a plurality of individual resistor segments arranged in width wise direction. These resistor segments may be coupled in series or parallel to provide a desired resistance value of the thick film resistor in question.

FIG. 2c) illustrates a vertical cross-sectional view of an infusion fluid warmer 250 in accordance with a third embodiment of the invention. Similar features and elements of the present embodiment and the above-described second embodiment of the infusion fluid warmer have been provided with corresponding reference numerals to ease comparison. An exterior casing shell 252 comprises a fluid inlet port 260, where the infusion fluid enters (illustrated by arrow 261), and an oppositely arranged fluid outlet port 258, where the infusion fluid exits enters (illustrated by arrow 263), during operation of the infusion fluid warmer 250. The housing shell 254 is encapsulated or enclosed within the outer or exterior casing shell 552 held together by an associated pair of cap nuts or caps 262, 264.

In the present infusion fluid warmer 250, the fluid channel comprises a first or upper channel segment 253a arranged between the upper wall structure 257 of the housing shell 254 and the upper wall structure of the exterior casing 252. A second channel segment 253b is arranged between the lower wall structure 255 of the housing shell 254 and an inwardly oriented surface of the lower wall structure of the exterior casing 252. In this manner, the fluid channel extends around the housing shell 254 instead of through the housing shell 204 as in the second embodiment described above. The upper and the lower wall structures 257, 255, may be separate parts that have been bonded after their fabrication. The housing shell 204 is preferably formed in a thermally conducting and electrically insulating material, preferably comprising a ceramic material such as Aluminium Oxide ($Al_2O_3$). The upper and lower fluid channels 253a, 253b preferably extends below a substantial portion of the facing surfaces of the upper and lower exterior casing to maximize a flow rate of the infusion fluid flow through the fluid channels. Likewise, the direct physical contact between the infusion fluid and the upper and lower wall structures 257, 255 through the facing surfaces is maximized to improve direct heat energy transfer to the infusion fluid through the upper and lower wall structures 257, 255. The straight channel or passage design of the upper and lower fluid channels 253a, 253b leads to a small pressure drop.

An array of thick film resistors 256a-256d acts as a heating element of the infusion fluid warmer 250. The array of thick film resistors 206a-206d is screen-printed, or firmly bonded or attached with an alternative fasting mechanism, on surfaces of the upper and lower wall structures, 257, 255, respectively, facing away from the fluid channels 253a, 253b. The upper array of thick film resistors 206a-206b is bonded to the upper wall structure 257 and faces the lower array of thick film resistors 206c-206d bonded to the lower wall structure 255 such that a small intermediate volume is formed there between. The upper and lower wall structures, 257, 255u are preferably sealing bonded to each other such that infusion fluid is prevented from entering the small intermediate volume and short-circuit the thick film resistors. The array of thick film resistors 256a-256d is preferably bonded to the upper and lower wall structures 207, 205 such that efficient thermal coupling, i.e. low thermal resistance, is achieved to the respective wall structures and therefore also to the infusion fluid flowing in the upper and lower fluid channels 253a, 253b. As described above, the individual resistors of the array of thick film resistors are preferably arranged in abutment with the wall structure in question without any intervening air gap to ensure efficient heat transfer from the array of thick film resistors 206a-206d through the upper and lower wall structures, 257, 255 to the infusion fluid.

The skilled person will appreciate the firm bonding between the array of thick film resistors 256a-256d and the housing shell 254 provides a compact unitary assembly of heating element and heat exchanger with a low parts count in the present infusion fluid warmer 250.

FIG. 2d) shows a top view of the infusion fluid warmer 250 in accordance with the third embodiment of the invention. The lid or upper wall of the thermoplastic casing 252 has been removed such that the outer surface of the upper wall 257 of the housing shell 254 is exposed. The thick film resistors 206a, 206b are disposed on the inner surface of the upper wall 207 facing away from the upper fluid channel. The thick film resistors 206a, 206b are covering a large portion of the available surface area of the upper wall 257. Each of the thick film resistors 206a, 206b comprises a plurality of individual resistor segments arranged in width wise direction. These resistor segments may be coupled in series or parallel to provide a desired resistance value of the thick film resistor in question.

Figure 3:
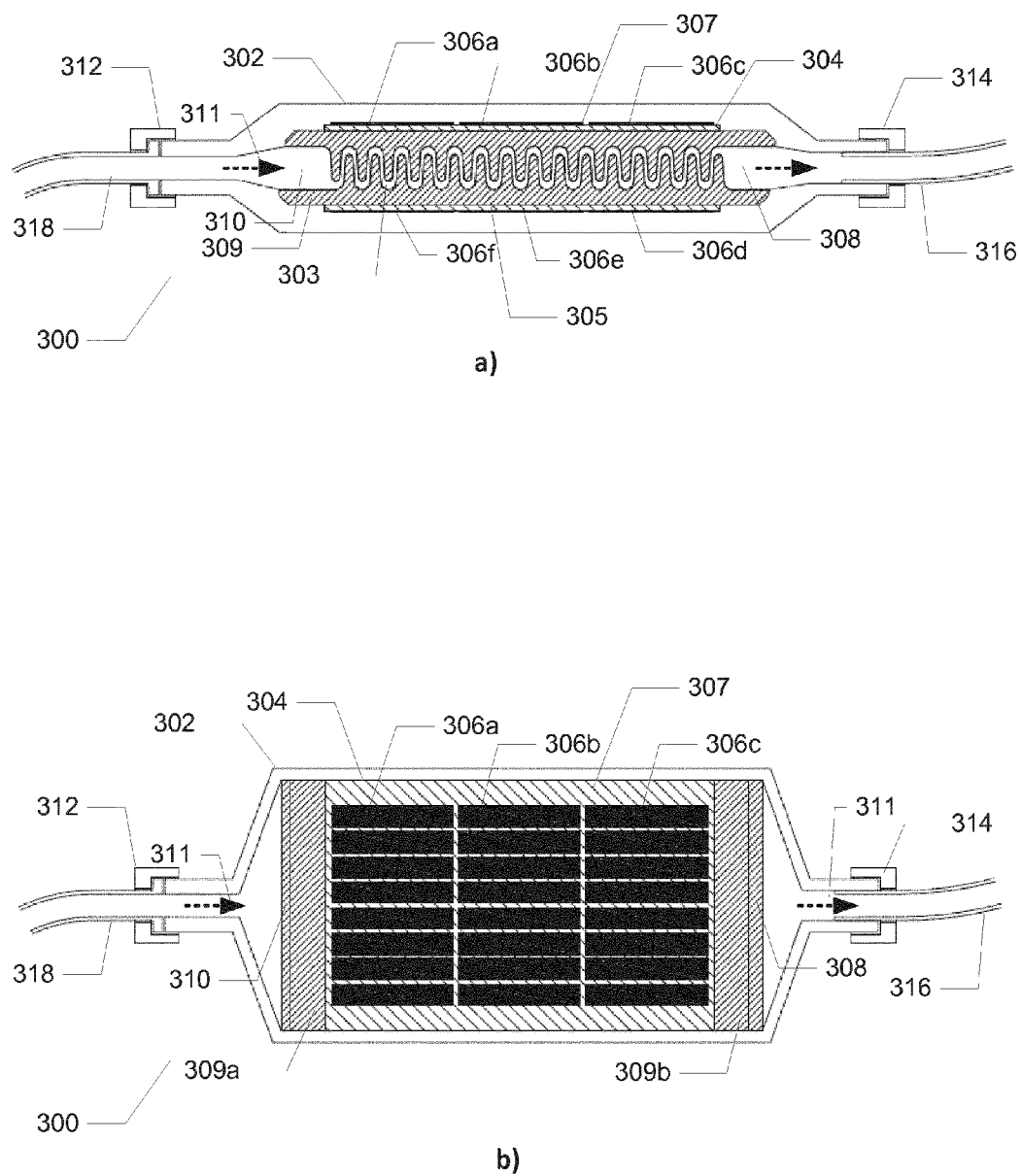

FIG. 3a) shows a vertical cross-sectional view of an infusion fluid warmer 300 in accordance with a third embodiment of the invention. Similar features in the present embodiment and the above-described first embodiment of the infusion fluid warmer have been provided with corresponding reference numerals to ease comparison. The infusion fluid warmer 300 comprises a housing shell 304 formed in a thermally conducting and electrically insulating material, preferably comprising a ceramic material such as Aluminium Oxide ($Al_2O_3$). The dimensions of the housing shell 304 may vary in accordance with specific requirements for the infusion fluid warmer 300, in particular its fluid warming capacity. The housing shell 304 is encapsulated or enclosed within an outer casing 302 and its associated pair of cap nuts or caps 312, 314 which may be formed in one of the previously described materials and for the same purpose. The housing shell 304 comprises a plate shaped upper wall structure 307 and a separate lower, opposing, plate shaped wall structure 305. An aluminium heat exchanger 309 is sandwiched in-between the plate shaped upper and lower wall structures 307, 305, respectively, and thermally coupled thereto for example by direct physical contact or through a layer of a suitable thermal compound. A fluid channel 303 is formed in the metallic heat exchanger 309 such that infusion fluid is brought in physical contact with the metallic heat exchanger to receive heat energy therefrom. The upper wall structure 307 and the lower wall structure 305 may be bonded or fastened to opposing sides of the metallic heat exchanger 309 by any suitable means and manufacturing processes such as gluing, soldering, press-fitting, welding etc. Thick film resistors 306a, 306b and 306c are screen-printed on an outer surface of the upper wall structure 307 facing oppositely to the metallic heat exchanger 309 and thick film resistors 306d, 306e and 306f are screen-printed on an outer surface of the lower wall structure 307 facing oppositely to the metallic heat exchanger 309 in which a fluid channel 303 is formed. The fluid channel 303 extends between a fluid inlet port 310 and a fluid outlet port 308 arranged in the metallic heat exchanger 309. The fluid channel 303 has a meandering shape similar to the shape in the above-described first embodiment of the infusion fluid warmer. The fluid channel 303 preferably extends below a substantial portion of the width of the upper and lower wall structures 307, 305 to improve an infusion fluid flow rate through the fluid channel 303. Likewise, the direct physical contact area between the infusion fluid and the upper and lower wall structures 307, 305 inside the fluid channel 303 is maximized to improve heat energy transfer. The height of the fluid channel 303 preferably lies between 0.1 mm and 5 cm. A significant advantage of the metallic heat exchanger 309 is its lower thermal resistance compared to e.g. ceramic material whereby the fluid warming capacity is increased allowing higher fluid flow rate. The metallic heat exchanger 309 also increases the surface area and the mechanical strength of the housing shell 304 albeit at the expense of size and complexity of the infusion fluid warmer.

FIG. 3b) shows a top view of the infusion fluid warmer 300 in accordance with the third embodiment of the invention. The lid, or upper wall of the thermoplastic casing 302 has been removed such that the outer surface of the upper wall 307 of the housing shell 304 is exposed. Edge segments of the metallic heat exchanger 309 protrude or project lengthwise to the outside of the upper surface 307 of the ceramic housing shell 304. The fluid inlet port 310 is formed beneath the left side edge segment 309a and the fluid outlet port is formed beneath the right side edge segment 309b. The thick film resistors 306a, 306b, 306c are disposed on the outer surface of the upper wall 307 covering a large portion of the available surface area. Each of the thick film resistors 306a, 306b, 306c comprises a plurality of individual resistor segments arranged in width wise direction. These resistor segments may be coupled in series or parallel to provide a desired resistance value of the thick film resistor in question. Since the thick film resistors 306a, 306b, 306c are in good thermal contact with the upper wall structure 307, which in turn is in good thermal contact with the metallic heat exchanger 309, heat energy dissipated in the thick film resistors 306a, 306b, 306c is efficiently transmitted or coupled to the infusion fluid in the fluid channel 303.

FIG. 4a) shows a vertical cross-sectional view of an infusion fluid warmer 400 in accordance with a forth embodiment of the invention. Similar features in the present embodiment and the above-described first embodiment of the infusion fluid warmer have been provided with corresponding reference numerals to ease comparison. The infusion fluid warmer 400 comprises a housing shell 404 formed in a thermally conducting and electrically insulating material, preferably comprising a ceramic material such as Aluminium Oxide ($Al_2O_3$). The dimensions of the housing shell 404 may vary in accordance with specific requirements for the infusion fluid warmer 400, in particular its fluid warming capacity. The housing shell 404 is encapsulated or enclosed within an outer casing 402 and its associated pair of cap nuts or caps 412, 414 which may be formed in one of the previously described materials and for the same purpose. The housing shell 404 comprises a rectangular plate shaped upper wall structure 407 and a separate rectangular lower, opposing, plate shaped wall structure 405. An aluminium heat exchanger 409 is sandwiched in-between the plate shaped upper and lower wall structures 407, 405, respectively, and thermally coupled thereto for example by direct physical contact or through a layer of a suitable thermal compound. The aluminium heat exchanger 409 has a rectangular structure with flat upper and lower surfaces mating to the plate shaped upper and lower wall structures 407, 405 to allow good thermal coupling (i.e. low thermal resistance) between these parts. A straight fluid channel 403 with rectangular cross-sectional profile extends centrally through the metallic heat exchanger 409 such that infusion fluid is brought in physical contact with the metallic heat exchanger 409 to receive heat energy therefrom. The upper wall structure 407 and the lower wall structure 405 may be bonded or fastened to opposing sides of the metallic heat exchanger 409 by any suitable fastening process such as gluing, soldering, press-fitting, welding etc. Thick film resistors 406a, 406b are screen-printed on an outer surface of the upper wall structure 407 facing oppositely to the metallic heat exchanger 409 and thick film resistors 406c, 406d are screen-printed on an outer surface of the lower wall structure 405 facing oppositely to the metallic heat exchanger 409 in which a fluid channel 403 is formed. The fluid channel 403 extends between a fluid inlet port or slit 410 and a fluid outlet port or slit 408 arranged in the metallic heat exchanger 409. The fluid channel 403 preferably extends below a substantial portion of the width of the upper and lower wall structures 407, 405 to improve an infusion fluid flow rate through the fluid channel 403. Likewise, a direct physical contact area between the infusion fluid and the upper and lower wall structures of the fluid channel 403 is maximized to improve heat energy transfer. The height of the fluid channel 403 preferably lies between 0.1 mm and 5 cm. A significant advantage of the straight channel form of the present metallic heat exchanger 409 compared to the above-described meandering fluid channel shape in the metallic heat exchanger 309 is its smaller pressure drop. The metallic heat exchanger 409 also increases the surface area and the mechanical strength of the housing shell 404.

FIG. 4b) shows a top view of the infusion fluid warmer 400 in accordance with the fourth embodiment of the invention. The lid or upper wall structure of the thermoplastic casing 402 has been removed such that the outer surface of the upper wall 407 of the ceramic housing shell 404 is exposed. The upper wall 407 covers the underlying metallic heat exchanger 403. The fluid inlet port 410 is formed as a rectangular slit in a central portion of the metallic heat exchanger 409 and the fluid outlet port 408 is likewise formed as a rectangular slit in the central portion of the metallic heat exchanger 409 in its opposite end. The thick film resistors 406a, 406b are disposed, preferably screen-printed, on the outer surface of the upper wall 407 covering a large portion of the available surface area. Each of the thick film resistors 406a, 406b comprises a plurality of individual resistor segments arranged in width wise direction. These resistor segments may be coupled in series or parallel to provide a desired resistance value of the thick film resistor in question. Since the thick film resistors 406a, 406b are in good thermal contact with the upper wall structure 407, which in turn is in good thermal contact with the metallic heat exchanger 409, heat energy dissipated in the thick film resistors 406a, 406b is efficiently transmitted to the infusion fluid in the fluid channel 403. Naturally, the same kind of efficient heat energy transfer is made from the thick film resistors 406c, 406d to the infusion fluid.

Figure 5:
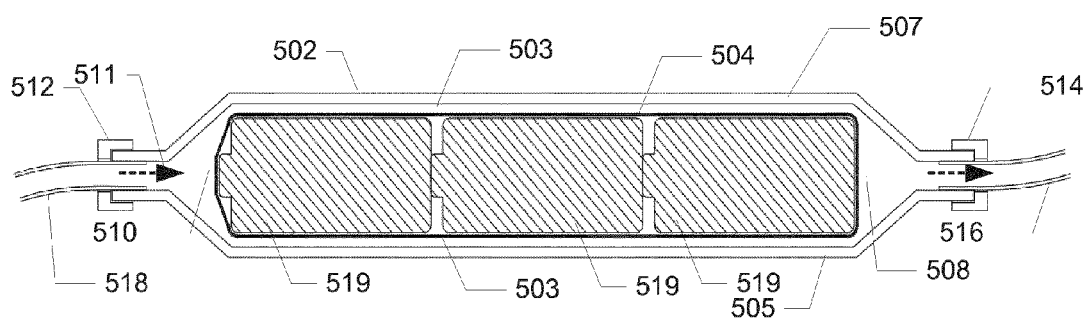
FIG. 5 shows a vertical cross-sectional view of a battery powered infusion fluid warmer in accordance with a sixth embodiment of the invention.

FIG. 5 shows a vertical cross-sectional view of a battery powered infusion fluid warmer 500 in accordance with the previously discussed second and separate aspect of the invention wherein the heating element comprises a portable energy source such as one or more rechargeable batteries, non-rechargeable batteries, super capacitors etc. The infusion fluid warmer 500 comprises an outer casing 502 which may be formed in a suitable polymeric material for example a thermoplastic material or elastomeric compound by injection moulding. The outer casing 502 may be shaped and sized to protect a battery housing or shell 504 from mechanical shocks and impacts. A pair of cap nuts or caps 512, 514 covers respective entrance openings of the outer casing 502 and is preferably used to seal or isolate the interior volume of the outer casing 502 from liquids, dust and other pollutants in the external environment. The dimensions of the outer casing 502 may vary in accordance with specific requirements for the infusion fluid warmer 500, in particular its fluid warming capacity.

The outer casing 502 has a cylindrical shape with a semi-cylindrical upper wall structure 507 and a lower, opposing, semi-cylindrical wall structure 505. The battery shell 504 is preferably formed in a thermally conducting and electrically insulating material such as a ceramic material for example Aluminium Oxide ($Al_2O_3$) to electrically insulate three rechargeable batteries 519a, 519b, 519c from a fluid channel 503. The battery shell 504 preferably has a cylindrical shape conforming to an inner contour of the outer casing 502 but with a cross-sectional diameter sufficiently small to leave an annular cylindrical passage 503 between the inner surface of the outer casing 502 and the battery shell 504. The annular cylindrical passage 503 forms a fluid channel or passage extending horizontally between a fluid inlet port 510 and a fluid output port 508 to allow a flow of infusion fluid through the outer casing 502. The skilled person will understand that the three rechargeable batteries 519a, 519b, 519c could be have numerous other shapes than cylindrical and the shapes of the battery shell 504 and outer casing 502 adapted thereto. In one such embodiment, each of the rechargeable batteries has a rectangular cross-sectional profile and the fluid channel 503 has a corresponding cross-sectional profile. The skilled person will understand that the separate battery shell 504 which encloses the three rechargeable batteries may be superfluous in other embodiments of the portable infusion fluid warmer. In these other embodiments, each outer casing of the rechargeable batteries may possess a thermally conducting and electrically insulating property and therefore brought in direct contact with the infusion fluid. The cold or unheated infusion fluid such as blood or IV solution flows from a fluid source such as fluid bag through an IV line or tube 518 through the fluid inlet port 510, through the fluid channel 503 at out of the fluid outlet port 508. From the fluid outlet port 508, heated or warmed infusion fluid flows through the IV line or tube 516 towards an IV-catheter (e.g. Venflon) inserted in a patient's vessel for the purpose of intravenous therapy. The rechargeable batteries 519a, 519b, 519c act like heating elements in accordance with the present embodiment of the invention. The outer surface of the battery shell 504 conducts heat energy generated by the batteries to the infusion fluid in the fluid channel 503 because of the direct physical contact between the outer surface of the battery shell 504 and the (flowing) infusion fluid. The rechargeable batteries 519a, 519b, 519c are preferably in good thermal contact with the battery shell 504 for example by means of a direct physical contact or by means of a thermal contact through an intervening layer of thermal compound or an intervening layer of solid material with good thermal conductivity.

The infusion fluid warmer 500 preferably comprises a temperature sensor (not shown) for determining a temperature of the infusion fluid in the fluid channel 503 for example at the outlet port 508 to ascertain the infusion fluid temperature lies within a certain allowable range for example between 36 and 37 degree Celsius. A controller circuit (not shown) is operatively coupled to determine or set a discharge current drawn from the 3 rechargeable batteries 519a, 519b, 519c so as to control the instantaneous amount of power dissipated internally within the rechargeable batteries 519a, 519b, 519c due to their respective internal impedances. This internal power dissipation in the rechargeable batteries 519a, 519b, 519c leads to the generation of heat energy which is thermally coupled to the infusion fluid through the thermally conducting battery shell 504 as explained above. In this manner, the infusion fluid is warmed or heated by excess heat generated by the rechargeable batteries 519a, 519b, 519c instead of wasting excess heat to the surrounding air such that efficient use is made of energy stored in the rechargeable batteries 519a, 519b, 519c. The controller circuit may use temperature data from the temperature sensor to control the instantaneous power dissipation internally within the rechargeable batteries such that a desired infusion fluid temperature at the outlet port is maintained during delivery of the infusion fluid to the patient.

The skilled person will understand that the above-outlined use of internal power dissipation of the rechargeable batteries 519a, 519b, 519c to heat the infusion fluid may be supplemented with a separate heating element such as the previously described arrays of thick film resistors. The array of thick film resistors could be screen-printed on a suitable inner surface area (i.e. on the opposite side of the fluid channel) of the battery shell 504 such as to be electrically insulated from the infusion fluid, in particular if the battery shell material comprises a suitable ceramic material.

In this manner, efficient use is made of both power dissipated in the array of thick film resistors and internal power dissipation in the rechargeable batteries. The controller circuit preferably comprises a programmable microprocessor such as a Digital Signal Processor and suitable program code or instructions implementing the control algorithm as previously described.

The invention claimed is:

1. An infusion fluid warmer comprising:
    a casing shell having an upper wall structure and a lower, opposing, wall structure; said casing shell enclosing:
    a fluid channel extending through the casing;
    fluid inlet and outlet ports coupled to opposite ends of the fluid channel to allow a flow of infusion fluid through the casing shell;
    a housing shell formed in a thermally conducting and electrically insulating material and comprising a plate shaped upper wall structure and an opposing plate shaped lower wall structure;
    a first heating element bonded to the plate shaped upper wall structure and thermally coupled thereto;
    a second heating element bonded to the plate shaped lower wall structure and thermally coupled thereto, and
    an aluminum heat exchanger sandwiched between the plate shaped upper wall structure and the opposing plate shaped lower wall structure and thermally coupled to the plate shaped upper wall structure and plate shaped lower wall structure,
    wherein a straight portion of the fluid channel possesses a rectangular cross-sectional profile and extends through the aluminum heat exchanger such that heat energy is transferred to the infusion fluid by direct physical contact with aluminum heat exchanger material,
    wherein the first heating element is bonded to a surface of the plate shaped upper wall structure facing away from the straight portion of the fluid channel and the second heating element is bonded to a surface of the plate shaped lower wall structure facing away from the fluid channel, and
    wherein at least one surface of the plate shaped upper and lower wall structures facing away from the fluid channel comprises a pair of electrical coupling terminals for receipt of electrical power to the first heating element or the second heating element.

2. An infusion fluid warmer according to claim 1, wherein the first and second heating elements comprise portable energy sources.

3. An infusion fluid warmer according to claim 2, wherein a thermal resistance between the portable energy source and the fluid channel is less than 100° C./W.

4. An infusion fluid warmer according to claim 2, wherein a thermal resistance between the portable energy source and the fluid channel is less than 25° C./W.

5. An infusion fluid warmer according to claim 2, wherein a thermal resistance between the portable energy source and the fluid channel is less than 10° C./W.

6. An infusion fluid warmer according to claim 1, wherein the housing shell has a flat plate shaped structure with a height less than 2.0 cm.

7. An infusion fluid warmer according to claim 1, wherein the housing shell comprises a ceramic material selected from the group consisting of Aluminum oxide ($Al_2O_3$), Aluminum Nitrate, and Beryllium Oxide.

8. An infusion fluid warmer according to claim 1, wherein the first heating element or the second heating element comprises a thick film or thin film resistor.

9. An infusion fluid warmer according claim 8, wherein the temperature sensor comprises a thick film resistor or thin film resistor of the first or second heating elements.

10. An infusion fluid warmer according to claim 1, wherein the housing shell has a flat plate shaped structure with a height less than 1.0 cm.

11. An infusion fluid warmer according to claim 1, wherein a height of the straight portion of the fluid channel is between 0.1 mm and 5 cm.

12. An infusion fluid warmer according to claim 1, further comprising:
    a temperature sensor for determining a temperature of the infusion fluid in the fluid channel; and
    a controller circuit operatively coupled to the temperature sensor and to the first and second heating elements to control instantaneous power dissipation of the first and second heating elements;
    wherein the controller circuit is adapted to adjust power dissipation in the first and second heating elements in accordance with a desired or target temperature of the infusion fluid based on temperature data from the temperature sensor.

13. An infusion fluid warmer according to claim 12, wherein the controller circuit comprises one or more semiconductor transistors and/or semiconductors diodes delivering a modulated drive signal to the first and second heating elements to adjust the instantaneous power dissipated therein.

14. An infusion fluid warmer according claim 12, wherein the temperature sensor comprises a thick film resistor or thin film resistor of the first or second heating elements.

* * * * *